United States Patent [19]

Shiba et al.

[11] Patent Number: 4,804,378
[45] Date of Patent: Feb. 14, 1989

[54] ABSORBENT ARTICLE

[75] Inventors: Daisuke Shiba; Akira Sakurai; Iwao Miyashita, all of Utsunomiya, Japan

[73] Assignee: KAO Corporation, Tokyo, Japan

[21] Appl. No.: 42,216

[22] Filed: Apr. 24, 1987

[30] Foreign Application Priority Data

May 7, 1986 [JP] Japan .................. 61-104015

[51] Int. Cl.⁴ .................. A61F 13/16; B32B 27/00
[52] U.S. Cl. .................. 604/367; 604/378; 604/372; 428/286; 428/298
[58] Field of Search .................. 604/378, 374, 375, 367, 604/358, 385, 372, 377, 400; 428/298, 286, 287, 913

[56] References Cited

U.S. PATENT DOCUMENTS

| 4,216,772 | 8/1980 | Tsuchiya et al. | 604/377 X |
| 4,217,900 | 8/1980 | Wiegner et al. | 604/377 X |
| 4,372,310 | 2/1983 | Sergeant | 604/377 X |
| 4,603,070 | 7/1986 | Steel et al. | 604/378 X |
| 4,652,484 | 3/1987 | Shiba et al. | 428/298 X |

Primary Examiner—Stephen C. Pellegrino
Attorney, Agent, or Firm—Birch, Stewart, Kolasch & Birch

[57] ABSTRACT

An absorbing article comprises a surface layer to be in contact with skins containing from 60 to 100% by weight of first fibers having a hydrophilic surface and a hydrophobic inside and from 40 to 0% by weight of second fibers which are hydrophilic at least at their surface, and a rearface constituted at least with one or more layers containing from 0 to 50% by weight of said first fibers and from 100 to 50% by weight of said second fibers, in which the surface hydrophilic property, after being wetted, is higher in said second fibers than in said first fibers.

6 Claims, 1 Drawing Sheet

ABSORBENT ARTICLE

The invention relates to an absorbent article such as a sanitary napkin and a disposable diaper having an excellent absorption property. In particular, the invention relates to an improvement of a nonwoven fabric to use in the absorbent article.

The invention applies to an absorbent article comprising a nonwoven fabric and an absorbent such as fluff pulp, called also cotton-like pulp, an absorbing paper and an absorbent polymer. It may further comprise a leak-proof layer on the back side. The disposable diaper is called also a paper diaper.

Various performances are required for the non-woven fabrics constituting the surface layer of such absorbing articles and most important performances among them are restriction for the surface liquid flow upon discharge of urine or menstrual blood, which may lead to leakage, reduction for the return of liquid maintained in the absorbing layer to skins, comfortable feeling upon contact with skins, etc.

In the non-woven fabrics utilized so far for conventional absorbing articles, restriction for the surface liquid flow has generally been made, for example, with the use of regenerated hydrophilic fibers represented typically by rayons. However, the regenerated hydrophilic fibers are mixed solely or together with hydrophobic fibers uniformly into non-woven fabrics in the conventional constitutions and, since the surface of the hydrophobic fibers is water repellent, the mixing ratio of the regenerated hydrophilic fibers has to be increased extremely for providing sufficient hydrophilic property to the surface of the non-woven fabrics in the latter case. Therefore, the water absorbing rate at the surface of the non-woven fabrics can indeed be increased to thereby decrease the liquid flow at the surface but, since the regenerated hydrophilic fibers themselves absorb the water content to the inside thereof, have an intense water retaining power and show a great decrease of bulkiness upon wetting, the surface in contact with the skins becomes highly sticky and the liquid return from the absorbing layer to the skin is increased to result in problems such as worsened feeling upon use and occurrence of skin eruptions in sanitary napkins, paper diapers and like other application uses.

Recently, use of dry non-woven fabrics mainly composed of synthetic fibers has become popular remarkably as the surface material for the absorbing articles and the foregoing problems of the stickiness and remarkable liquid return inherent to the non-woven fabrics mainly composed of regenerated hydrophilic fibers have gradually been improved. However, since conventional dry non-woven fabrics made of hydrophobic fibers have a water repellent surface, they cause remarkable liquid flow and trend of liquid leakage. In addition, there has been an attempt to treat the hydrophobic fibers with a surface active agent thereby rendering the surface of the non-woven fabrics hydrophilic to restrict the liquid flow at the surface. However durability to water is insufficient if they are merely treated with the surface active agent and, after menstrual blood or urine has once permeated through them, the hydrophilic property at that portion is greatly reduced, in a case if the menstrual blood or urine is discharged at the same portion of the non-woven fabrics at the next time, the liquid is also liable to be flown thereby making it difficult to maintain the initial performance during the use of the absorbing article.

Further, as shown in Japanese Patent Laid-open No. 60-198151, it has also been attempted to treat the hydrophobic fibers having absorbed sweat or water with a high speed water stream to form non-woven fabrics thereby providing the durability to the hydrophilic property of the non-woven fabrics. However, there has been taken no considerations for the constitution of the fibers also in this case and, since the upper layer is mainly composed of hydrophobic fibers liquid tends to flow readily and, further, sweat absorbing and water absorbing aids at the surface of the fibers are washed out upon high speed water treatment, to greatly reduce the hydrophilic property of the non-woven fabrics upon practical use again failing to obtain a sufficient water absorbing rate.

Although improvements have been reported also in the commercially available articles, such as application of various water-absorbing high molecular materials as the absorbing material, it has not yet been found those capable of satisfying both the absorbing rate (surface liquid flow) and the liquid returning performance.

The prevent inventors have made an earnest study for improving the drawbacks in the non-woven fabrics used so far as the surface material for the conventional absorbing articles, that is, for finding non-woven fabrics capable of satisfying the conflicting performances that both of the absorbing rate and the liquid return are not worsened upon practical use and, as a result, have accomplished this invention.

Specifically, this invention concerns an adsorbing article using, as the surface material, those non-woven fabrics comprising a surface layer containing from 60 to 100% by weight of first fibers having a hydrophilic surface and a hydrophobic inside and from 40 to 0% by weight of second fibers which are hydrophilic at least at their surface, and a rearface constituted at least with one or more layers containing from 0 to 50% by weight of the first fibers and from 100 to 50% by weight of the second fibers, in which the surface hydrophilic property, after being wetted is higher in the second fibers than in the first fibers.

An absorbent article of the invention comprises as the surface material a nonwoven fabric comprising (1) a surface layer comprising 60 to 100 percent by weight of the first fibers having a hydrophilic surface portion and a hydrophobic inside portion and from 40 to zero percent by weight of the second fibers being hydrophilic at least on the surface thereof and (2) at least one back layer comprising from zero to 50 percent by weight of said first fibers and from 100 to 50 percent by weight of said second fibers, said second fibers having a larger surface hydrophilic property than said first fibers after having been wetted. It is preferred that the surface layer consists of the first fibers and the back layer consists of the second fibers. It is preferable that said first fibers have been formed by making hydrophobic fibers hydrophilic on the surface thereof and the second fibers are hydrophilic fibers or have been formed by making hydrophobic fibers hydrophilic on the surface thereof.

It is preferred that the first fibers of the surface layer, wetted, has a surface hydrophilic property of 0.5 ml or smaller and the second fibers of the back layer, wetted, has that of 1 to 2 ml.

The absorbent article of the invention may comprise said nonwoven fabric, an absorbent and a leak-proof material and may be a sanitary napkin or a disposable diaper.

The first fibers referred to herein also include a mixture of two or more kinds of different hydrophobic fibers in which the surface hydrophilic property after wetting are low at the similar extent. In the same way, the second fibers referred to herein also include a mixture of two or more kinds of different hydrophobic fibers in which the surface hydrophilic property after wetting are higher to a similar extent than that of the first fibers described above.

In order that the non-woven fabrics can rapidly introduce liquid such as body fluids to the absorbing layer, it is necessary that the surface of the fibers constituting the non-woven fabrics is sufficiently hydrophilic at least in the situation where the absorbing article is constituted with the non-woven fabrics. However, since the liquid once absorbed in the absorbing layer is liable to return to the outside through the nonwoven fabrics if the hydrophilic property at the surface of the fibers is excessively high, it is necessary that at least the surface layer of the non-woven fabrics to be in contact with the skins is rather reduced with the surface hydrophilic property due to the passage of water. In order to provide the surface layer of the non-woven fabrics with such a property, it is necessary that the weight ratio of the first fibers, that is, the fibers having the hydrophilic property at the surface and the hydrophobic property at the inside and low water retainability of the fibers per se, in which the hydrophilic property after wetting is reduced as compared with that before the wetting, is at least greater than 60% by weight and, most preferably, 100% in the surface layer.

The hydrophilic property of the first fibers after wetting (Hw) is preferably less than 0.5 ml, more preferably, less than 0.3 ml according to the test method for water absorption amount as described later in examples.

Then, it is necessary that the liquid absorbing rate at the surface of the non-woven fabrics is not reduced even if the surface hydrophilic property is lowered due to the passage of water. For this purpose, it is necessary for the presence of a rearface layer comprising at least one layer having hydrophilic property at least at the surface which is not reduced so much after wetting, with the weight ratio of the second fibers having the surface hydrophilic property after wetting higher than that of the first fibers, being greater than that in the surface layer. In this case, for obtaining an effect that the liquid absorbing rate at the surface of the non-woven fabrics is not reduced even if the surface hydrophilic property is lowered due to the passage of water, it is necessary that the weight ratio of the second fibers constituting the rearface layer is at least more than 50% and it may be 100% so long as the fiber constituting the surface layer lies within the range described above.

Then, for attaining the purpose of maintaining the absorbing rate more effectively, it is desirable that the hydrophilic property of the second fibers after wetting (Hw) corresponds to more than 1 ml by the test method for the water absorption amount described later in the examples. Further, for reducing the liquid return, it is better that the second fibers also have a hydrophilic surface and a hydrophobic inside and the water retainability of the fibers per se is lower and, most desirably, all of the second fibers are made of such fibers. Further, it is more preferable that the hydrophilic property of the second fibers after wetting corresponds to less than 2 ml according to the the test method for the water absorption amount as described later in the examples. For the application use to usual sanitary napkins, paper diapers and the likes, it may be sufficient that the rearface layer is a single layer but it may be a multi-layered structure in such application use requiring great thickness.

The first fibers and the second fibers may be different from each other with respect to the surface layer and the rearface layer and it is desirable that the degree of the difference in the hydrophilic property between the first fibers and the second fibers is high because it reduces the liquid return.

The first fibers and the second fibers as described above can be prepared by applying a hydrophilic treatment to the surface of hydrophobic fibers and further controlling the durability of the hydrophilic treatment to the water content. Further, it is only necessary for the second fibers that they have hydrophilic property at least at the surface and those having hydrophilic property till the inside such as rayon fibers may also be used.

The method of applying the surface hydrophilic treatment to the hydrophobic fibers can include, for example, a method of rendering hydrophilic property to the surface of hydrophobic synthetic fibers such as polyolefinic fibers, for example, of polyethylene and polypropylene, polyester fibers, polyamide fibers and polyacrylonitrile fibers using a surface active agent. Alternatively, the surface may be rendered hydrophilic by applying a surface chemical treatment such as chemically bonding those chemical materials having hydrophilic groups such as monomers having hydrophilic groups or polymers having hydrophilic groups, or a physical surface modification such as plasma fabrication and incorporation of chemical material having hydrophilic groups by kneading. For the chemical surface modification, those chemical materials having hydrophilic groups may be chemically bonded with the fiber surface, or chemical materials having hydrophilic groups may be bonded and crosslinked to each other to cover the surface of the fibers. Further, it is also possible to improve the water absorbing property by making the shape of the hydrophobic fibers into a profile configuration, or applying a hydrophilic treatment to the surface of them.

Since the method of surface hydrophilic treatment can control the durability to the water content by adequately selecting the processing conditions with the agent for giving surface hydrophilic property or fabrication conditions for the fibers, they may be applied to the first fibers and the second fibers. Among them, for the first fibers, hydrophilic treatment using a surface active agent can provide easy control for the durability against water content and an economical advantage in view of the cost as well. For the hydrophilic treatment to the surface of the hydorphobic fibers, a method of giving hydrophilic property in the production step of the fibers is customary but, as another example, nonwoven fabrics may be prepared by using the hydrophobic synthetic fibers described above, and the hydrophilic property may be given to the surface of the hydrophobic fibers by applying chemical and physical surface modifications or the treatment with a solution of a surface active agent as the after fabrication.

For the hydrophobic fibers, polyesters which can be applied with various kinds of surface treatment and are less expensive in view of the cost are suitable to both the first fibers and the second fibers. Furthermore, for the first fibers, the polyolefinic fibers which can be easily applied with the hydrophilic treatment with low durability by a surface active agent and which are effective also as the thermo-fusible binder are also suitable.

In accordance with the fiber composition and the layer constitution as described above, the non-woven fabrics can provide those performances of rapidly absorbing the liquid into the absorbing layer and restricting the return of liquid from the absorbing layer that conflict to each other can be obtained simultaneously.

Then, descriptions will be made specifically below for the conditions to attain the foregoing properties of the non-woven fabrics most effectively.

The thickness of non-woven fabrics constitutes one of the major factors for the return of liquid from the absorbing layer to the outside of the non-woven fabrics. That is, if the thickness of the non-woven fabrics is decreased excessively, distance between the skin and the absorbing layer is extremely reduced when the absorbing article is put on under wet state to increase the liquids return and significantly worsen the feeling upon use. On the other hand, if the thickness of the non-woven fabrics is increased, the liquid return is surely decreased. However, if the thickness is excessively large, the entire absorbing article becomes thick, to bring about abnormal feeling to users and also result in a problems of increased manufacturing cost. Further, if the thickness of the surface layer is excessively large, the thickness is increased at a portion where the hydrophobic property is increased than that under dry state once after the permeation of the water content through the non-woven fabrics, and it is difficult for the water content dropped in the next time to intrude to the inside of the non-woven fabrics.

In this way, it is necessary that the thickness of the non-woven fabrics lies within a most adequate range in view of the liquid-returning property, feeling upon use and production cost. The range of the adequate thickness varies depending on the application uses and the entire thickness is desirablly from 0.3 mm to 0.8 mm under the load of 2.5 g/cm$^2$ when using the non-woven fabrics for the application uses of sanitary napkin and from 0.6 to 2.5 mm in the case of using them for the paper diapers.

In order that the non-woven fabrics have the thickness as described above, it is necessary to adequately select the fibers for constituting the non-woven fabrics and provide the non-woven fabrics with an appropriate weight per unit area. At first, it is necessary to use hydrophobic synthetic fibers having a surface rendered hydrophilic which show no remarkable reduction in the bulkiness upon wetting as has been described above. The size of the fibers may be within a range from 1.5 to 6 denier, because it is difficult to increase the bulkiness of the entire non-woven fabrics if the size is less than 1.5 denier, whereas the entire non-woven fabrics become rigid to worsen the feelings if the size exceeds 6 denier. Further, although higher weight per unit area is generally preferable for providing the non-woven fabrics with the bulkiness, it is desired on the other hand to suppress the weight per area as low as possible when the production cost is taken into consideration. Accordingly, it is preferable that the fibers has elasticity as high as possible, which can be attained, for example, by a method of avoiding the use of extremely fine fibers as described above or selecting hollow fibers or those fibers applied with sterical crimping.

Thus, if the easy control of the durability to water content of the surface hydrophilic treatment, reduction in the weight, easy of attaining the high elasticity and easy fabrication to non-woven fabrics are taken into consideration, polyester and polyolefin type fibers are most suitable as the fibers for non-woven fabrics.

Referring to the weight per unit of the non-woven fabrics, since the thickness is reduced as the weight per unit area is lower, whereas the thickness is increased as the weight per unit goes higher as a general trend, there is also an adequate range depending on the application uses. In the case where the fibers as described above used, the weight is desirably within the range from 10 to 30 g/m$^2$ as a whole and from 5 to 10 g/m$^2$ for the surface layer in the case of using them as sanitary napkins, whereas from 20 to 50 g/m$^2$ as a whole and from 7 to 15 g/m$^2$ for the surface layer in the case of using them as paper diapers.

Referring finally to the method of stabilized webs, any of the methods can optionally be selected provided that they have such a nature that the surface hydrophilic property of the constituent fibers is greater in the second fibers than in the first fibers in the situation where the nonwoven fabrics are finally formed. However, in the case where the hydrophilic treatment to the fiber surface undergoes damages in the course of forming the non-woven fabrics as in the entanglement by the high speed water flow, the hydrophilic property has to be provided by the after-treatment as described above, which requires much labors and brings about an extreme difficulty. Accordingly, for forming the non-woven fabrics without degrading the hydrophilic property of the starting fiber material, it is desirable to set the fibers to each other by the thermal fusion of the fibers. Further, the method of forming the non-woven fabrics stabilized by the fusion of the fibers is excellent as compared with other methods also in that the fabrics have sterically stabilized skeltons and can attain the physical property (thickness, feelings) of the non-woven fabrics as described above efficiency (with no remarkable increase in the weight per unit area).

Figure 1:
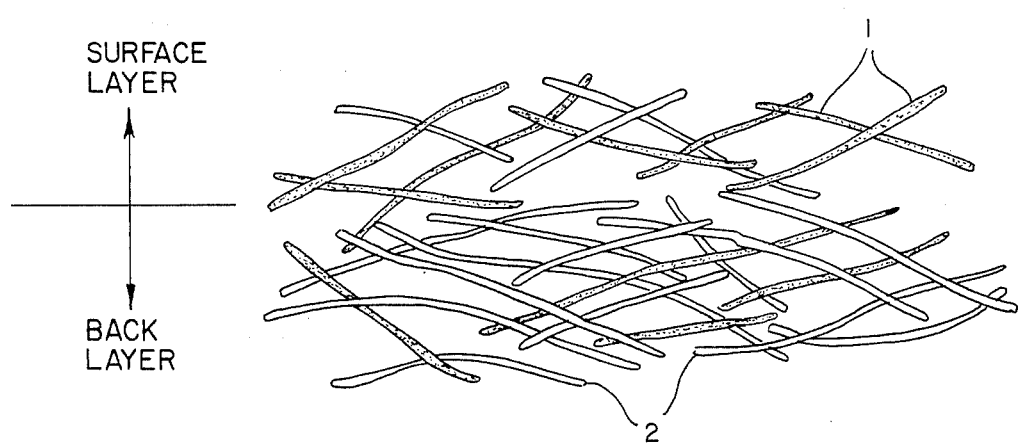
FIG. 1 is a cross sectional view of the nonwoven fabric used in the present invention. The nonwoven fabric comprises first fibers 1 having a hydrophilic surface portion and a hydrophobic central portion and second fibers 2 being hydrophilic at least in the surface thereof.

This invention will now be described in more details by way of the examples.

EXAMPLE 1-17 AND COMPARATIVE EXAMPLE 1-7

(Fibers and non-woven fibers)

Using fibers shown in Table 1 as the first fibers and the second fibers, various kinds of non-woven fabrics shown in Tables 2 and 3 were manufactured.

The method of processing the fibers with the agent providing hydrophilic property (hereinafter simply as a hydrophilic agent) shown in Table 1 are as below:

(A) Fibers were immersed in an aqueous solution of a surface active agent and then dewatered and dried.

(B) The hydrophilic agent was dispersed in a solvent, into which the fibers were immersed, then dewatered and dried followed by heat treatment (140° C. for 30 minutes).

(C) The hydrophilic agent was dispersed in a solvent, into which the fibers immersed, then dewatered and dried followed by heat treatment (170° C. for 10 minutes).

(D) The procedures were according to Example 1 of Japanese Patent Laid-Open No. Sho 55-122074.

(E) After placing fibers in a bell jar made of glass and evacuating the inside of the bell jar to lower than 10 Torr, an exhaust valve was closed and air was supplied up to 0.1 mmHg. Then, vapors of the hydrophilic agent were supplied up to 0.5% based on the weight of the fibers and high frequency voltage (13.56 MHz) was applied to electrodes for about 3 minutes.

(F) Commercially available fibers were used as they are.

(G) Commercially available fibers were used as they are.

(H) Commercially available fibers were used as they are.

(I) Commercially available polyethylene - polypropylene composite fibers were washed with warmed water, dewatered and then dried.

In Examples 1-16 and Comparative Examples 1-6, non-woven fabrics were manufactured by way of heat bonding method (passing a hot blow at 140° C. to a card web and setting ES fibers to other fibers through fusing by using polyethylene—polypropylene composite fibers)(ES fibers) or low melting polyester—polyester composite fibers (Melty) as binder fibers. In Example 17, fibers of the web were entangled under a high pressure water flow (spray pressure at 55 kg/cm$^2$, average amount of water stream supplied in the lateral direction: 250 cc/cm.min) to form non-woven fabrics. Then, after applying the same hydrophilic processing as in (B) above, the hydrophilic agent described in (A) above was sprayed from the side of the first layer and then dried. In Comparative Example 7, the fiber webs were subjected to the high pressure water flow processing under the same conditions as described above into non-woven fabrics, which were not applied with the hydrophilic treatment by the after treatment.

(Specimens for Measurement)

Commercially available sanitary napkins (trade name; Lorie, manufactured by Kao Co) and disposable paper diapers (trade name Merries, manufactured by Kao Co.) were used while removing non-woven fabrics therefrom and, instead, placing non-woven fabrics shown in Tables 2 and 3 thereover respectively as the specimens to be measured as absorbing articles assuming the sanitary napkins and disposable paper diapers. Examples 1-7, Examples 9-17 and Comparative Examples 1-7 were used for the sanitary napkins, while Example 8 was used for the disposable paper diapers.

(Test Method)

(1) Surface liquid flow

Test solution was dropped from above 1 cm of the surface of the specimen inclined by 45° and the flowing distance along the surface of the non-woven fabrics from the point of dropping to the point where the solution was absorbed to the inside of the specimen was measured, which was defined as the surface liquid flow for the first time. Then, one minute after the dropping of the test solution, the test solution was again dropped to a portion where the solution had been dropped previously and the flowing distance along the surface of the non-woven fabrics from the point of dropping to the point where the solution was absorbed to the inside of the specimen was measured, which was defined as the surface liquid flow for the second time. Those showing short surface liquid flow for the first time and the surface liquid flow for the second time showing no considerable change indicate that there was no remarkable lateral leak. The dropping condition was 0.1 g/sec for the specimen assuming the sanitary napkins and 0.5 g/cm for the specimen assuming the paper diapers.

(2) Returning amount

The test solution was caused to be absorbed by 10 cc in the specimens assuming the sanitary napkin and by 150 cc in the specimens assuming the paper diaper, pressure was applied after a predetermined of time and the amount of the test solution returned from the inside through the non-woven fabrics was measured. As the returning amount is smaller, surface stickiness is reduced, the feeling upon use is better and wiping effect is more excellent.

(3) Water absorption amount

Using the apparatus as shown in FIG. 1, in which fiber webs 1 were packed at a density of 0.13 g/cm$^3$ into a glass tube 2 of 14 mm inner diameter, ion exchanged water 5 was caused to be absorbed through a glass filter 4 into the fiber webs under a constant hydraulic pressure (atmospheric pressure) in a head portion 3 and the water absorption amount (ml) after one minutes was measured. The water absorption amount in the dry state is defined as Hd, while the water absorption amount after passing 600 cc of the ion exchanged water through the fiber webs and then dried was defined as Hw. Greater Hw means higher surface hydrophilic property after wetting.

TABLE 1

| | Hydrophobic agent | Fiber Kind of fiber | Composition | Manufacturer | Remarks |
|---|---|---|---|---|---|
| (A) | Surface active agent (mixture of alkyl ether sulfate and alkyl phosphate) | ES(i,Aj) | Polyethylene-polypropylene composite fiber | Chisso-polypro fiber Co. | Trade name (ES) |
| | | SP(i,Aj) | Polypropylene-polyester composite fiber | Daiwa Boseki Co. | Trade name (NBF) |
| | | LPET(i,Aj) | Low melting polyester-polyester composite fiber | Unitika Ltd. | Trade name (Melty) |
| (B) | Polyoxyalkylene group-containing polyester oligomer | PET(i,Bj) | Polyester | Teijin Co. | Hollow cross section |
| (C) | Hydrophilic copolymer type epoxy modified silicone | PET(i,Cj) | Polyester | Teijin Co. | |
| | | Ac(i,Cj) | Acrylic | Toho Rayon Co. | |
| | | Ny(i,Cj) | Nylon | Unitika Ltd. | |
| (D) | Polyvinyl alcohol resin | PET(i,Dj) | Polyester | Teijin Co. | Profiled cross |

TABLE 1-continued

| | Hydrophobic agent | Fiber Kind of fiber | Composition | Manufacturer | Remarks |
|---|---|---|---|---|---|
| (E) | Plasma polymerization of hydroxyethyl methacrylate | PP(i,Ej) | Polypropylene | Daiwa Boseki Co. | section |
| (F) | Porous fiber | Ac(i,Fj) | Acrylic | Nippon Gosei Do. | Trade name (Aqualon) |
| (G) | Hydrophilic agent-kneaded fiber | PET(i,Gj) | Polyester | Kanebo Co. | Trade name (aquabell) |
| (H) | | Ray(i,Hj) | Rayon | Daiwa Boseki Co. | |
| (I) | Degreased with warm water | ES(i,Ij) | Polyethylene-polypropylene composite fiber | Chisso-polypro Fiber Co. | Trade name (ES) |

(Note 1): Used as first fiber when i = 1, and as second fiber when i = 2
(Note 2): j represents denier
(Note 3): Ray(i,Hj) undergoes no hydrophilic treatment

TABLE 2

| Example | No. | Entire weight/area g/m² | Surface layer Weight area g/m² | Fiber | Mixing ratio % | Rearface layer Weight area g/m² | fiber | Mixing ratio % |
|---|---|---|---|---|---|---|---|---|
| Comparative Example | 1 | 20 | 8 | ES (1,I2) | 100 | 12 | Ray (2,H3) | 100 |
| Comparative Example | 2 | 20 | 8 | Ray (2,H3) | 100 | 12 | Ray (2,H3) | 100 |
| Comparative Example | 3 | 20 | 8 | ES (1,I2) Ray (2,H3) | 50 50 | 12 | Ray (2,H3) | 100 |
| Comparative Example | 4 | 20 | 8 | ES (1,I2) Ray (2,H3) | 60 40 | 12 | Ray (2,H3) | 100 |
| Example | 1 | 20 | 8 | ES (1,A2) Ray (2,H3) | 60 40 | 12 | Ray (2,H3) | 100 |
| Example | 2 | 20 | 8 | ES (1,A2) PET (2,B3) | 60 40 | 12 | PET (2,B6) | 100 |
| Example | 3 | 20 | 8 | ES (1,A2) PET (2,B3) | 80 20 | 12 | PET (2,B6) | 100 |
| Example | 4 | 20 | 8 | ES (1,A2) | 100 | 12 | PET (2,B6) | 100 |
| Example | 5 | 20 | 8 | ES (1,A2) | 100 | 12 | ES (1,A2) PET (2,B6) | 35 65 |
| Example | 6 | 20 | 8 | ES (1,A2) | 100 | 12 | ES (1,A2) PET (2,B6) | 50 50 |
| Comparative Example | 5 | 20 | 8 | ES (1,A2) | 100 | 12 | ES (1,A2) PET (2,B6) | 70 30 |
| Comparative Example | 6 | 20 | 8 | ES (1,A2) PET (2,B3) | 50 50 | 12 | ES (1,A2) PET (2,B6) | 50 50 |
| Example | 7 | 20 | 8 | ES (1,A2) PET (2,B3) | 60 40 | 12 | ES (1,A2) PET (2,B6) | 50 50 |
| Example | 8 | 35 | 10 | ES (1,A2) | 100 | 20 | ES (1,A2) PET (2,B6) | 50 50 |

| Example | No. | Surface liquid flow First mm | Surface liquid flow Second mm | Returning amount g | Water absorption amount First fiber Hd (ml) | First fiber Hw (ml) | second fiber Hd (ml) | second fiber Hw (ml) |
|---|---|---|---|---|---|---|---|---|
| Comparative Example | 1 | 150 | 150 | 0.5 | 0 | 0 | 4.7 | 4.5 |
| Comparative Example | 2 | 20 | 20 | 6.8 | | | 4.7 | 4.5 |
| Comparative Example | 3 | 68 | 62 | 4.9 | 0 | 0 | 4.7 | 4.5 |
| Comparative Example | 4 | 87 | 80 | 4.2 | 0 | 0 | 4.7 | 4.5 |
| Example | 1 | 20 | 18 | 4.7 | 2.2 | 0.1 | 4.7 | 4.5 |
| Example | 2 | 24 | 26 | 3.1 | 2.2 | 0.1 | 2.5 (B3) 2.3 (B6) | 2.7 (B3) 2.6 (B6) |
| Example | 3 | 24 | 27 | 2.5 | 2.2 | 0.1 | 2.5 (B3) 2.3 (B6) | 2.7 (B3) 2.6 (B6) |
| Example | 4 | 26 | 30 | 2.2 | 2.2 | 0.1 | 2.3 | 2.6 |
| Example | 5 | 25 | 33 | 2 | 2.2 | 0.1 | 2.3 | 2.6 |
| Example | 6 | 25 | 32 | 1.5 | 2.2 | 0.1 | 2.3 | 2.6 |
| Comparative Example | 5 | 25 | 41 | 1.5 | 2.2 | 0.1 | 2.3 | 2.6 |
| Comparative Example | 6 | 24 | 32 | 3.1 | 2.2 | 0.1 | 2.5 (B3) 2.3 (B6) | 2.7 (B3) 2.6 (B6) |
| Example | 7 | 25 | 35 | 2.6 | 2.2 | 0.1 | 2.5 (B3) 2.3 (B6) | 2.7 (B3) 2.6 (B6) |
| Example | 8 | 26 | 35 | 1.5 | 2.2 | 0.1 | 2.3 | 2.6 |

TABLE 3

| | Entire weight/area | Surface layer Weight/area | Mixing ratio | Rearface layer Weight/area | Mixing ratio |
|---|---|---|---|---|---|

TABLE 3-continued

| Example | No. | g/m² | g/m² | Fiber | % | g/m² | fiber | % |
|---|---|---|---|---|---|---|---|---|
| Example | 9 | 20 | 8 | ES (1,A2) | 100 | 12 | ES (1,A2) | 35 |
|  |  |  |  |  |  |  | PET (2,C3) | 65 |
| Example | 10 | 20 | 8 | ES (1,A2) | 100 | 12 | ES (1,A2) | 35 |
|  |  |  |  |  |  |  | Ac (2,C3) | 65 |
| Example | 11 | 20 | 8 | ES (1,A2) | 100 | 12 | ES (1,A2) | 35 |
|  |  |  |  |  |  |  | Ny (2,C1.5) | 65 |
| Example | 12 | 20 | 8 | ES (1,A2) | 100 | 12 | ES (1,A2) | 35 |
|  |  |  |  |  |  |  | PET (2,D3) | 65 |
| Example | 13 | 20 | 8 | ES (1,A2) | 100 | 12 | ES (1,A2) | 35 |
|  |  |  |  |  |  |  | PP (2,E2) | 65 |
| Example | 14 | 20 | 8 | ES (1,A2) | 100 | 12 | ES (1,A2) | 35 |
|  |  |  |  |  |  |  | Ac (2,F6) | 65 |
| Example | 15 | 20 | 8 | ES (1,A2) | 100 | 12 | ES (1,A2) | 35 |
|  |  |  |  |  |  |  | PET (2,G3) | 65 |
| Example | 16 | 20 | 8 | LPET (1,A4) | 100 | 12 | LPET (1,A4) | 35 |
|  |  |  |  |  |  |  | PET (2,B6) | 65 |
| Example | 17 | 20 | 8 | SP (1,A3) | 100 | 12 | PET (2,B6) | 100 |
| Comparative Example | 7 | 20 | 8 | ES (1,A2) | 60 | 12 | ES (1,A2) | 50 |
|  |  |  |  | PET (2,B3) | 40 |  | PET (2,B6) | 50 |

| Example | No. | Surface liquid flow First mm | Surface liquid flow Second mm | Returning amount g | Water absorption amount First fiber Hd (ml) | Water absorption amount First fiber Hw (ml) | Water absorption amount Second fiber Hd (ml) | Water absorption amount Second fiber Hw (ml) |
|---|---|---|---|---|---|---|---|---|
| Example | 9 | 21 | 37 | 1.8 | 2.2 | 0.1 | 1.9 | 1.5 |
| Example | 10 | 23 | 36 | 1.4 | 2.2 | 0.1 | 1.7 | 1.4 |
| Example | 11 | 28 | 35 | 1.5 | 2.2 | 0.1 | 2 | 1.5 |
| Example | 12 | 22 | 30 | 1.5 | 2.2 | 0.1 | 2.6 | 1.8 |
| Example | 13 | 26 | 35 | 1.7 | 2.2 | 0.1 | 2.1 | 1.6 |
| Example | 14 | 24 | 35 | 1.6 | 2.2 | 0.1 | 1.5 | 1.9 |
| Example | 15 | 24 | 32 | 1.4 | 2.2 | 0.1 | 1.4 | 1.8 |
| Example | 16 | 24 | 35 | 1.6 | 0.4 | 0.1 | 2.3 | 1.9 |
| Example | 17 | 29 | 36 | 1.3 | 2.4 | 0.1 | 2.3 | 1.9 |
| Comparative Example | 7 | 150 | 150 | 0.5 | 0 | 0 | 0.5 (B3) 0.7 (B6) | 0.6 (B3) 0.5 (B6) |

(Effect of the Invention)

As can be seen from Examples, the surface liquid flow in the absorbing articles according to this invention is low both at the first and the second times and the liquid return from the inside to the surface is also low.

In Comparative Examples 1-7, absorbing articles were manufactured and the surface liquid flow and the liquid return thereof were measured by using the nonwoven fabrics out of the range according to this invention and by the same procedures as in Examples. Since fibers having no substantial hydrophilic property were used for the surface layers in Comparative Example 1, 3 and 4, the surface liquid flow is high and leakage is liable to be caused. In Comparative Example 2 is constituted up to 100% with fibers which are hydrophilic at the surface and the inside and the returning amount is remarkable and stickiness is liable to occur although the surface liquid flow is preferable.

In Examples 2-17 and Comparative Examples 5 and 6, the fabrics are constituted with fibers having a hydrophilic surface and a hydrophobic inside and show lower returning amount as compared with Example 1 comprising fibers having hydrophilic surface and inside. However, Comparative Example 5, among them, has a lower mixing ratio of the second fibers in the rearface layer than that defined in this invention and the surface liquid flow at the second time is increased. Further, in Comparative Example 6, the mixing ratio of the second fibers in the surface layer is greater than the range as defined in this invention and, accordingly, the returning amount is increased.

In Comparative Example 7, the surface hydrophilic treatment undergoes damage by the high speed water flow to remarkably reduce the hydrophilic property and, as a result, the surface liquid flow is increased.

What is claimed is:

1. An absorbent article which comprises as the surface material a nonwoven fabric comprising
   (1) a surface layer comprising 60 to 100 percent by weight of first fibers having a hydrophilic surface portion and a hydrophobic inside portion and from 40 to zero percent by weight of the second fibers being hydrophilic at least on the surface thereof and
   (2) at least one back layer comprising from zero to 50 percent by weight of said first fibers and from 100 to 50 percent by weight of said second fibers,
   said second fibers having a larger surface hydrophilic property than said first fibers after having been wetted.

2. An absorbent article as claimed in claim 1, in which the surface layer consists of the first fibers.

3. An absorbent articles as claimed in claim 1, in which said first fibers have been formed by making hydrophobic fibers hydrophilic on the surface thereof and the second fibers are hydrophilic fibers or have been formed by making hydrophobic fibers hydrophilic on the surface thereof.

4. An absorbent articles as claimed in claim 1, in which the first fibers of the surface layer, wetted, has a surface hydrophilic property of 0.5 ml or smaller and the second fibers of the back layer, wetted, has that of 1 to 2 ml.

5. An absorbent article as claimed in claim 1, which comprises said nonwoven fabric, an absorbent and a leak-proof material.

6. An absorbent article as claimed in claim 1, which is a sanitary napkin or a disposable diaper.

* * * * *